(12) United States Patent
Gannoe et al.

(10) Patent No.: US 8,062,207 B2
(45) Date of Patent: *Nov. 22, 2011

(54) INTRA-GASTRIC FASTENING DEVICES

(75) Inventors: Jamy Gannoe, Redwood City, CA (US);
Gary Weller, Los Gatos, CA (US);
Craig Gerbi, Mountain View, CA (US);
Douglas S. Sutton, Pacifica, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1466 days.

This patent is subject to a terminal disclaimer.

(21) Appl. No.: 11/129,626

(22) Filed: May 13, 2005

(65) Prior Publication Data

US 2005/0222592 A1 Oct. 6, 2005

Related U.S. Application Data

(63) Continuation of application No. 10/394,832, filed on Mar. 21, 2003, now Pat. No. 6,994,715, which is a continuation of application No. 10/215,070, filed on Aug. 7, 2002, now Pat. No. 6,746,460.

(51) Int. Cl.
*A61F 2/00* (2006.01)
(52) U.S. Cl. ............................ 600/37; 606/153; 606/192
(58) Field of Classification Search .................. 606/139, 606/144, 148, 151, 153, 191–195; 600/37
See application file for complete search history.

(56) References Cited

U.S. PATENT DOCUMENTS

| 2,108,206 A | 2/1938 | Meeker |
| 2,508,690 A | 7/1948 | Schmerl |
| 3,372,443 A | 3/1968 | Daddona, Jr. |
| 3,395,710 A | 8/1968 | Stratton et al. |
| 3,986,493 A | 10/1976 | Hendren, III |
| 4,057,065 A | 11/1977 | Thow |

(Continued)

FOREIGN PATENT DOCUMENTS

EP 0 137 878 A1 4/1985

(Continued)

OTHER PUBLICATIONS

Büchler, M.W., M.D. et al., *A Technique for Gastroplasty As a Substitute for the Esophagus: Fundus Rotation Gastroplasty*, Journal of the American College of Surgeons, vol. 182, pp. 241-245, Mar. 1996.

(Continued)

*Primary Examiner* — Darwin Erezo
(74) *Attorney, Agent, or Firm* — Nutter McClennen & Fish LLP

(57) ABSTRACT

Intra-gastric fastening devices are disclosed herein. Expandable devices that are inserted into the stomach of the patient are maintained within by anchoring or otherwise fixing the expandable devices to the stomach walls. Such expandable devices, like inflatable balloons, have tethering regions for attachment to the one or more fasteners which can be configured to extend at least partially through one or several folds of the patient's stomach wall. The fasteners are thus affixed to the stomach walls by deploying the fasteners and manipulating the tissue walls entirely from the inside organ. Such fasteners can be formed in a variety of configurations, e.g., helical, elongate, ring, clamp, and they can be configured to be non-piercing. Alternatively, sutures can be used to wrap around or through a tissue fold for tethering the expandable devices. Non-piercing biased clamps can also be used to tether the device within the stomach.

10 Claims, 7 Drawing Sheets

U.S. PATENT DOCUMENTS

| | | | |
|---|---|---|---|
| 4,063,561 A | 12/1977 | McKenna | |
| 4,133,315 A | 1/1979 | Berman et al. | |
| 4,134,405 A | 1/1979 | Smit | |
| 4,198,982 A | 4/1980 | Fortner et al. | |
| 4,246,893 A | 1/1981 | Berson | |
| 4,258,705 A | 3/1981 | Sorensen et al. | |
| 4,311,146 A | 1/1982 | Wonder | |
| 4,315,509 A | 2/1982 | Smit | |
| 4,343,066 A | 8/1982 | Lance | |
| 4,402,445 A | 9/1983 | Green | |
| 4,416,267 A * | 11/1983 | Garren et al. | 128/898 |
| 4,458,681 A | 7/1984 | Hopkins | |
| 4,485,805 A | 12/1984 | Foster, Jr. | |
| 4,501,264 A | 2/1985 | Rockey | |
| 4,547,192 A | 10/1985 | Brodsky et al. | |
| 4,558,699 A | 12/1985 | Bashour | |
| 4,592,339 A | 6/1986 | Kuzmak et al. | |
| 4,598,699 A | 7/1986 | Garren et al. | |
| 4,607,618 A | 8/1986 | Angelchik | |
| 4,610,383 A | 9/1986 | Rothfuss et al. | |
| 4,636,205 A | 1/1987 | Steer | |
| 4,641,653 A | 2/1987 | Rockey | |
| 4,643,169 A | 2/1987 | Koss et al. | |
| 4,646,722 A | 3/1987 | Silverstein et al. | |
| 4,648,383 A | 3/1987 | Angelchik | |
| 4,671,287 A | 6/1987 | Fiddian-Green | |
| 4,694,827 A | 9/1987 | Weiner et al. | |
| 4,716,900 A | 1/1988 | Ravo et al. | |
| 4,723,547 A | 2/1988 | Kullas et al. | |
| 4,739,758 A | 4/1988 | Lai et al. | |
| 4,744,363 A | 5/1988 | Hasson | |
| 4,773,393 A | 9/1988 | Haber et al. | |
| 4,790,294 A | 12/1988 | Allred, III et al. | |
| 4,795,430 A | 1/1989 | Quinn et al. | |
| 4,803,985 A | 2/1989 | Hill | |
| 4,841,888 A * | 6/1989 | Mills et al. | 112/169 |
| 4,899,747 A | 2/1990 | Garren et al. | |
| 4,905,693 A | 3/1990 | Ravo | |
| 4,925,446 A | 5/1990 | Garay et al. | |
| 4,927,428 A | 5/1990 | Richards | |
| 4,969,474 A | 11/1990 | Schwarz | |
| 5,037,021 A | 8/1991 | Mills et al. | |
| 5,059,193 A | 10/1991 | Kuslich | |
| 5,080,663 A | 1/1992 | Mills et al. | |
| 5,084,061 A | 1/1992 | Gau et al. | |
| 5,112,310 A | 5/1992 | Grobe | |
| 5,129,915 A | 7/1992 | Cantenys | |
| 5,156,609 A | 10/1992 | Nakao et al. | |
| 5,171,233 A | 12/1992 | Amplatz et al. | |
| 5,197,649 A | 3/1993 | Bessler et al. | |
| 5,220,928 A | 6/1993 | Oddsen et al. | |
| 5,222,961 A | 6/1993 | Nakao et al. | |
| 5,226,429 A | 7/1993 | Kuzmak | |
| 5,234,454 A | 8/1993 | Bangs | |
| 5,246,456 A | 9/1993 | Wilkinson | |
| 5,248,302 A | 9/1993 | Patrick et al. | |
| 5,250,058 A | 10/1993 | Miller et al. | |
| 5,254,126 A | 10/1993 | Filipi et al. | |
| 5,259,366 A | 11/1993 | Reydel et al. | |
| 5,259,399 A | 11/1993 | Brown | |
| 5,261,920 A | 11/1993 | Main et al. | |
| 5,263,629 A | 11/1993 | Trumbull et al. | |
| 5,297,536 A | 3/1994 | Wilk | |
| 5,301,658 A | 4/1994 | Zhu et al. | |
| 5,306,300 A | 4/1994 | Berry | |
| 5,309,896 A | 5/1994 | Moll et al. | |
| 5,309,927 A | 5/1994 | Welch | |
| 5,327,914 A | 7/1994 | Shlain | |
| 5,330,486 A | 7/1994 | Wilk | |
| 5,330,503 A | 7/1994 | Yoon | |
| 5,331,975 A | 7/1994 | Bonutti | |
| 5,334,209 A | 8/1994 | Yoon | |
| 5,334,210 A | 8/1994 | Gianturco | |
| 5,345,949 A | 9/1994 | Shlain | |
| 5,346,501 A | 9/1994 | Regula et al. | |
| 5,355,897 A | 10/1994 | Pietrafitta et al. | |
| 5,376,095 A | 12/1994 | Ortiz | |
| 5,382,231 A | 1/1995 | Shlain | |
| 5,403,312 A | 4/1995 | Yates et al. | |
| 5,403,326 A * | 4/1995 | Harrison et al. | 606/139 |
| 5,411,508 A | 5/1995 | Bessler et al. | |
| 5,433,721 A | 7/1995 | Hooven et al. | |
| 5,437,291 A | 8/1995 | Pasricha et al. | |
| 5,449,368 A | 9/1995 | Kuzmak | |
| 5,452,837 A | 9/1995 | Williamson, IV et al. | |
| 5,458,131 A | 10/1995 | Wilk | |
| 5,465,894 A | 11/1995 | Clark et al. | |
| 5,467,911 A | 11/1995 | Tsuruta et al. | |
| 5,486,183 A | 1/1996 | Middleman et al. | |
| 5,489,058 A | 2/1996 | Plyley et al. | |
| 5,503,635 A | 4/1996 | Sauer et al. | |
| 5,527,319 A | 6/1996 | Green et al. | |
| 5,535,935 A | 7/1996 | Vidal et al. | |
| 5,542,949 A | 8/1996 | Yoon | |
| 5,549,621 A | 8/1996 | Bessler et al. | |
| 5,551,622 A | 9/1996 | Yoon | |
| 5,555,898 A | 9/1996 | Suzuki et al. | |
| 5,558,665 A | 9/1996 | Kieturakis | |
| 5,571,116 A | 11/1996 | Bolanos et al. | |
| 5,577,654 A | 11/1996 | Bishop | |
| 5,578,044 A | 11/1996 | Gordon et al. | |
| 5,582,616 A | 12/1996 | Bolduc et al. | |
| 5,584,861 A | 12/1996 | Swain et al. | |
| 5,588,579 A | 12/1996 | Schnut et al. | |
| 5,601,604 A | 2/1997 | Vincent | |
| 5,603,443 A | 2/1997 | Clark et al. | |
| 5,607,094 A | 3/1997 | Clark et al. | |
| 5,624,381 A | 4/1997 | Kieturakis | |
| 5,626,588 A | 5/1997 | Sauer et al. | |
| 5,639,008 A | 6/1997 | Gallagher et al. | |
| 5,649,937 A | 7/1997 | Bito et al. | |
| 5,651,769 A | 7/1997 | Waxman et al. | |
| 5,655,698 A | 8/1997 | Yoon | |
| 5,662,664 A | 9/1997 | Gordon et al. | |
| 5,662,667 A | 9/1997 | Knodel | |
| 5,667,520 A | 9/1997 | Bonutti | |
| 5,676,659 A | 10/1997 | McGurk | |
| 5,676,674 A | 10/1997 | Bolanos et al. | |
| 5,685,868 A | 11/1997 | Lundquist | |
| 5,690,656 A | 11/1997 | Cope et al. | |
| 5,697,943 A | 12/1997 | Sauer et al. | |
| 5,707,382 A | 1/1998 | Sierocuk et al. | |
| 5,722,990 A | 3/1998 | Sugarbaker et al. | |
| 5,728,178 A | 3/1998 | Buffington et al. | |
| 5,735,848 A | 4/1998 | Yates et al. | |
| 5,749,893 A | 5/1998 | Vidal et al. | |
| 5,755,730 A | 5/1998 | Swain et al. | |
| 5,766,216 A | 6/1998 | Gangal et al. | |
| 5,776,054 A | 7/1998 | Bobra | |
| 5,782,844 A | 7/1998 | Yoon et al. | |
| 5,788,715 A | 8/1998 | Watson, Jr. et al. | |
| 5,792,153 A * | 8/1998 | Swain et al. | 606/144 |
| 5,810,851 A | 9/1998 | Yoon | |
| 5,810,855 A | 9/1998 | Rayburn et al. | |
| 5,810,882 A | 9/1998 | Bolduc et al. | |
| 5,816,471 A | 10/1998 | Plyley et al. | |
| 5,820,584 A | 10/1998 | Crabb | |
| 5,824,008 A | 10/1998 | Bolduc et al. | |
| 5,827,298 A | 10/1998 | Hart et al. | |
| 5,833,690 A | 11/1998 | Yates et al. | |
| 5,836,311 A | 11/1998 | Borst et al. | |
| 5,839,639 A | 11/1998 | Sauer et al. | |
| 5,860,581 A | 1/1999 | Robertson et al. | |
| 5,861,036 A | 1/1999 | Godin | |
| 5,868,141 A | 2/1999 | Ellias | |
| 5,868,760 A | 2/1999 | McGuckin, Jr. | |
| 5,876,448 A | 3/1999 | Thompson et al. | |
| 5,879,371 A | 3/1999 | Gardiner et al. | |
| 5,887,594 A | 3/1999 | LoCicero, III | |
| 5,888,196 A | 3/1999 | Bonutti | |
| 5,897,534 A | 4/1999 | Heim et al. | |
| 5,897,562 A | 4/1999 | Bolanos et al. | |
| 5,904,147 A | 5/1999 | Conlan et al. | |
| 5,906,625 A | 5/1999 | Bito et al. | |
| 5,910,105 A | 6/1999 | Swain et al. | |
| 5,910,149 A | 6/1999 | Kuzmak | |
| 5,921,993 A | 7/1999 | Yoon | |

| | | | | | | |
|---|---|---|---|---|---|---|
| 5,927,284 | A | 7/1999 | Borst et al. | 6,675,809 B2 * | 1/2004 | Stack et al. | 128/898 |
| 5,928,264 | A | 7/1999 | Sugarbaker et al. | 6,682,520 B2 | 1/2004 | Ingenito |
| 5,935,107 | A | 8/1999 | Taylor et al. | 6,689,062 B1 | 2/2004 | Mesallum |
| 5,938,669 | A | 8/1999 | Klaiber et al. | 6,692,485 B1 | 2/2004 | Brock et al. |
| 5,947,983 | A | 9/1999 | Solar et al. | 6,716,222 B2 | 4/2004 | McAlister et al. |
| 5,964,772 | A | 10/1999 | Bolduc et al. | 6,719,764 B1 * | 4/2004 | Gellman et al. | 606/145 |
| 5,964,782 | A | 10/1999 | Lafontaine et al. | 6,733,512 B2 | 5/2004 | McGhan |
| 5,972,001 | A | 10/1999 | Yoon | 6,736,822 B2 | 5/2004 | McClellan et al. |
| 5,972,002 | A | 10/1999 | Bark et al. | 6,740,098 B2 | 5/2004 | Abrams et al. |
| 5,976,161 | A | 11/1999 | Kirsch et al. | 6,740,121 B2 | 5/2004 | Geitz |
| 5,980,537 | A | 11/1999 | Ouchi | 6,746,460 B2 * | 6/2004 | Gannoe et al. | 606/153 |
| 5,993,464 | A | 11/1999 | Knodel | 6,746,489 B2 | 6/2004 | Dua et al. |
| 5,993,473 | A | 11/1999 | Chan et al. | 6,754,536 B2 | 6/2004 | Swoyer et al. |
| 6,015,378 | A | 1/2000 | Borst et al. | 6,755,849 B1 | 6/2004 | Gowda et al. |
| 6,030,364 | A | 2/2000 | Durgin et al. | 6,755,869 B2 | 6/2004 | Geitz |
| 6,030,392 | A | 2/2000 | Dakov | 6,756,364 B2 | 6/2004 | Barbier et al. |
| 6,042,538 | A | 3/2000 | Puskas | 6,764,518 B2 | 7/2004 | Godin |
| 6,044,847 | A | 4/2000 | Carter et al. | 6,773,440 B2 | 8/2004 | Gannoe et al. |
| 6,067,991 | A | 5/2000 | Forsell | 6,773,441 B1 | 8/2004 | Laufer et al. |
| 6,074,343 | A | 6/2000 | Nathanson et al. | 6,786,898 B2 | 9/2004 | Guenst |
| 6,083,241 | A | 7/2000 | Longo et al. | 6,790,214 B2 | 9/2004 | Kraemer et al. |
| 6,086,600 | A | 7/2000 | Kortenbach | 6,802,868 B2 | 10/2004 | Silverman et al. |
| 6,113,609 | A | 9/2000 | Adams | 6,821,285 B2 | 11/2004 | Laufer et al. |
| 6,119,913 | A | 9/2000 | Adams et al. | 6,835,199 B2 | 12/2004 | McGuckin, Jr. et al. |
| 6,120,513 | A | 9/2000 | Bailey et al. | 6,835,200 B2 | 12/2004 | Laufer et al. |
| 6,136,006 | A | 10/2000 | Johnson et al. | 6,837,848 B2 | 1/2005 | Bonner et al. |
| 6,159,146 | A | 12/2000 | El Gazayerli | 6,838,114 B2 | 1/2005 | Carpenter et al. |
| 6,159,195 | A | 12/2000 | Ha et al. | 6,840,423 B2 | 1/2005 | Adams et al. |
| 6,165,183 | A | 12/2000 | Kuehn et al. | 6,845,776 B2 * | 1/2005 | Stack et al. | 128/898 |
| 6,179,195 | B1 | 1/2001 | Adams et al. | 6,896,682 B1 | 5/2005 | McClellan et al. |
| 6,186,942 | B1 | 2/2001 | Sullivan et al. | 6,926,722 B2 | 8/2005 | Geitz |
| 6,186,985 | B1 | 2/2001 | Snow | 6,966,919 B2 | 11/2005 | Sixto, Jr. et al. |
| 6,197,022 | B1 | 3/2001 | Baker | 6,981,978 B2 | 1/2006 | Gannoe |
| 6,200,318 | B1 | 3/2001 | Har-Shai et al. | 6,991,643 B2 | 1/2006 | Saadat |
| 6,206,822 | B1 | 3/2001 | Foley et al. | 6,994,715 B2 * | 2/2006 | Gannoe et al. | 606/153 |
| 6,206,893 | B1 | 3/2001 | Klein et al. | 7,020,531 B1 | 3/2006 | Colliou et al. |
| 6,224,614 | B1 | 5/2001 | Yoon | 7,025,791 B2 | 4/2006 | Levine et al. |
| 6,231,561 | B1 | 5/2001 | Frazier et al. | 7,033,378 B2 | 4/2006 | Smith et al. |
| 6,248,058 | B1 | 6/2001 | Silverman et al. | 7,037,343 B2 | 5/2006 | Imran |
| 6,254,642 | B1 | 7/2001 | Taylor | 7,037,344 B2 | 5/2006 | Kagan et al. |
| 6,273,897 | B1 | 8/2001 | Dalessandro et al. | 7,063,715 B2 | 6/2006 | Onuki et al. |
| 6,279,809 | B1 | 8/2001 | Nicolo | 7,083,630 B2 | 8/2006 | DeVries et al. |
| 6,290,674 | B1 | 9/2001 | Roue et al. | 7,087,011 B2 | 8/2006 | Cabiri et al. |
| 6,293,923 | B1 | 9/2001 | Yachia et al. | 7,097,650 B2 | 8/2006 | Weller et al. |
| 6,302,917 | B1 | 10/2001 | Dua et al. | 2001/0014800 A1 | 8/2001 | Frazier et al. |
| 6,312,437 | B1 | 11/2001 | Kortenbach | 2001/0020190 A1 | 9/2001 | Taylor |
| 6,328,689 | B1 | 12/2001 | Gonzalez et al. | 2001/0037127 A1 | 11/2001 | De Hoyos Garza |
| 6,338,345 | B1 | 1/2002 | Johnson et al. | 2002/0022851 A1 | 2/2002 | Kalloo et al. |
| 6,352,543 | B1 | 3/2002 | Cole | 2002/0035361 A1 | 3/2002 | Houser et al. |
| 6,358,197 | B1 | 3/2002 | Silverman et al. | 2002/0040226 A1 | 4/2002 | Laufer et al. |
| 6,379,366 | B1 | 4/2002 | Fleischmann et al. | 2002/0047036 A1 | 4/2002 | Sullivan et al. |
| 6,387,104 | B1 | 5/2002 | Pugsley, Jr. et al. | 2002/0055757 A1 | 5/2002 | Torre et al. |
| 6,398,795 | B1 | 6/2002 | McAlister et al. | 2002/0058967 A1 | 5/2002 | Jervis |
| 6,416,535 | B1 | 7/2002 | Lazarus | 2002/0072761 A1 | 6/2002 | Abrams et al. |
| 6,423,087 | B1 | 7/2002 | Sawada | 2002/0077661 A1 | 6/2002 | Saadat |
| 6,432,040 | B1 | 8/2002 | Meah | 2002/0078967 A1 | 6/2002 | Sixto, Jr. et al. |
| 6,447,533 | B1 | 9/2002 | Adams | 2002/0082621 A1 | 6/2002 | Schurr et al. |
| 6,460,543 | B1 | 10/2002 | Forsell | 2002/0143346 A1 | 10/2002 | McGuckin, Jr. et al. |
| 6,475,136 | B1 | 11/2002 | Forsell | 2002/0165589 A1 | 11/2002 | Imran et al. |
| 6,478,791 | B1 * | 11/2002 | Carter et al. | 606/1 | 2002/0183768 A1 | 12/2002 | Deem et al. |
| 6,491,707 | B2 | 12/2002 | Makower et al. | 2002/0193816 A1 | 12/2002 | Laufer et al. |
| 6,494,888 | B1 | 12/2002 | Laufer et al. | 2003/0040804 A1 | 2/2003 | Stack et al. |
| 6,506,196 | B1 | 1/2003 | Laufer | 2003/0040808 A1 | 2/2003 | Stack et al. |
| 6,535,764 | B2 | 3/2003 | Imran et al. | 2003/0065340 A1 | 4/2003 | Geitz |
| 6,540,789 | B1 | 4/2003 | Silverman et al. | 2003/0065359 A1 | 4/2003 | Weller et al. |
| 6,551,310 | B1 | 4/2003 | Ganz et al. | 2003/0093117 A1 | 5/2003 | Saadat |
| 6,554,844 | B2 | 4/2003 | Lee et al. | 2003/0109892 A1 | 6/2003 | Deem et al. |
| 6,558,400 | B2 | 5/2003 | Deem et al. | 2003/0109931 A1 | 6/2003 | Geitz |
| 6,561,969 | B2 | 5/2003 | Frazier et al. | 2003/0109935 A1 | 6/2003 | Geitz |
| 6,572,629 | B2 | 6/2003 | Kalloo et al. | 2003/0120265 A1 | 6/2003 | Deem et al. |
| 6,579,301 | B1 | 6/2003 | Bales et al. | 2003/0120285 A1 | 6/2003 | Kortenbach |
| 6,592,596 | B1 | 7/2003 | Geitz | 2003/0120289 A1 | 6/2003 | McGuckin, Jr. et al. |
| 6,605,037 | B1 | 8/2003 | Moll et al. | 2003/0132267 A1 | 7/2003 | Adams et al. |
| 6,626,899 | B2 | 9/2003 | Houser et al. | 2003/0158563 A1 | 8/2003 | McClellan et al. |
| 6,626,916 | B1 | 9/2003 | Yeung et al. | 2003/0158601 A1 | 8/2003 | Silverman et al. |
| 6,632,227 | B2 | 10/2003 | Adams | 2003/0171760 A1 | 9/2003 | Gambale |
| 6,663,598 | B1 | 12/2003 | Carrillo, Jr. et al. | 2003/0208209 A1 | 11/2003 | Gambale et al. |
| 6,663,639 | B1 | 12/2003 | Laufer et al. | 2003/0225312 A1 | 12/2003 | Suzuki et al. |
| 6,663,640 | B2 | 12/2003 | Kortenbach | 2004/0006351 A1 | 1/2004 | Gannoe et al. |

| | | | |
|---|---|---|---|
| 2004/0009224 A1 | 1/2004 | Miller | |
| 2004/0010271 A1 | 1/2004 | Kortenbach | |
| 2004/0024386 A1 | 2/2004 | Deem et al. | |
| 2004/0034371 A1* | 2/2004 | Lehman et al. | 606/144 |
| 2004/0037865 A1 | 2/2004 | Miller | |
| 2004/0039452 A1 | 2/2004 | Bessler | |
| 2004/0049209 A1 | 3/2004 | Benchetrit | |
| 2004/0059349 A1 | 3/2004 | Sixto, Jr. et al. | |
| 2004/0059354 A1 | 3/2004 | Smith et al. | |
| 2004/0059358 A1 | 3/2004 | Kortenbach et al. | |
| 2004/0082963 A1 | 4/2004 | Gannoe et al. | |
| 2004/0087977 A1 | 5/2004 | Nolan et al. | |
| 2004/0089313 A1 | 5/2004 | Utley et al. | |
| 2004/0092892 A1 | 5/2004 | Kagan et al. | |
| 2004/0097989 A1 | 5/2004 | Molina Trigueros | |
| 2004/0107004 A1 | 6/2004 | Levine et al. | |
| 2004/0116949 A1 | 6/2004 | Ewers et al. | |
| 2004/0122456 A1 | 6/2004 | Saadat et al. | |
| 2004/0122473 A1 | 6/2004 | Ewers et al. | |
| 2004/0122526 A1 | 6/2004 | Imran | |
| 2004/0133147 A1 | 7/2004 | Woo | |
| 2004/0133238 A1 | 7/2004 | Cerier | |
| 2004/0138525 A1 | 7/2004 | Saadat | |
| 2004/0138526 A1 | 7/2004 | Guenst | |
| 2004/0138529 A1 | 7/2004 | Wiltshire et al. | |
| 2004/0138531 A1 | 7/2004 | Bonner et al. | |
| 2004/0138682 A1 | 7/2004 | Onuki et al. | |
| 2004/0147958 A1 | 7/2004 | Lam et al. | |
| 2004/0148021 A1 | 7/2004 | Cartledge et al. | |
| 2004/0148034 A1 | 7/2004 | Kagan et al. | |
| 2004/0158331 A1 | 8/2004 | Stack et al. | |
| 2004/0162568 A1 | 8/2004 | Saadat | |
| 2004/0167546 A1 | 8/2004 | Saadat et al. | |
| 2004/0172047 A1* | 9/2004 | Gellman et al. | 606/144 |
| 2004/0172141 A1 | 9/2004 | Stack et al. | |
| 2004/0181242 A1 | 9/2004 | Stack et al. | |
| 2004/0193190 A1 | 9/2004 | Liddicoat et al. | |
| 2004/0194157 A1 | 9/2004 | Meguid | |
| 2004/0194790 A1 | 10/2004 | Laufer et al. | |
| 2004/0210243 A1 | 10/2004 | Gannoe et al. | |
| 2004/0215180 A1 | 10/2004 | Starkebaum et al. | |
| 2004/0220682 A1 | 11/2004 | Levine et al. | |
| 2004/0225183 A1 | 11/2004 | Michlitsch et al. | |
| 2004/0225194 A1 | 11/2004 | Smith et al. | |
| 2004/0225305 A1 | 11/2004 | Ewers et al. | |
| 2004/0236357 A1 | 11/2004 | Kraemer et al. | |
| 2004/0249362 A1 | 12/2004 | Levine et al. | |
| 2005/0010162 A1 | 1/2005 | Utley et al. | |
| 2005/0021681 A1 | 1/2005 | Oommen | |
| 2005/0033328 A1 | 2/2005 | Laufer et al. | |
| 2005/0038415 A1 | 2/2005 | Rohr et al. | |
| 2005/0049718 A1 | 3/2005 | Dann et al. | |
| 2005/0055038 A1 | 3/2005 | Kelleher et al. | |
| 2005/0055039 A1 | 3/2005 | Burnett et al. | |
| 2005/0075622 A1 | 4/2005 | Levine et al. | |
| 2005/0075653 A1 | 4/2005 | Saadat et al. | |
| 2005/0080444 A1 | 4/2005 | Kraemer et al. | |
| 2005/0085787 A1 | 4/2005 | Laufer | |
| 2005/0096750 A1 | 5/2005 | Kagan et al. | |
| 2005/0119671 A1 | 6/2005 | Reydel et al. | |
| 2005/0143760 A1 | 6/2005 | Imran | |
| 2005/0148818 A1 | 7/2005 | Mesallum | |
| 2005/0149067 A1 | 7/2005 | Takemoto et al. | |
| 2005/0149114 A1 | 7/2005 | Cartledge et al. | |
| 2005/0177176 A1 | 8/2005 | Gerbi et al. | |
| 2005/0194038 A1 | 9/2005 | Brabec et al. | |
| 2005/0194294 A1 | 9/2005 | Oexle et al. | |
| 2005/0194312 A1 | 9/2005 | Niemeyer et al. | |
| 2005/0195925 A1 | 9/2005 | Traber | |
| 2005/0195944 A1 | 9/2005 | Bartels et al. | |
| 2005/0196356 A1 | 9/2005 | Leinen et al. | |
| 2005/0197540 A1 | 9/2005 | Liedtke | |
| 2005/0197622 A1 | 9/2005 | Blumenthal et al. | |
| 2005/0197684 A1 | 9/2005 | Koch | |
| 2005/0198476 A1 | 9/2005 | Gazsi et al. | |
| 2005/0203548 A1 | 9/2005 | Weller et al. | |
| 2005/0228415 A1 | 10/2005 | Gertner | |
| 2005/0256587 A1 | 11/2005 | Egan | |
| 2006/0020247 A1 | 1/2006 | Kagan et al. | |
| 2006/0020254 A1 | 1/2006 | Hoffmann | |
| 2006/0020276 A1 | 1/2006 | Saadat et al. | |
| 2006/0036267 A1 | 2/2006 | Saadat et al. | |

FOREIGN PATENT DOCUMENTS

| | | |
|---|---|---|
| EP | 0 174 843 A1 | 3/1986 |
| EP | 0 174 843 A2 | 3/1986 |
| EP | 0 246 999 A1 | 11/1987 |
| EP | 0 540 010 A2 | 5/1993 |
| JP | 63277063 | 11/1988 |
| JP | 63279854 | 11/1988 |
| JP | 63302863 | 12/1988 |
| JP | 1049572 | 2/1989 |
| JP | 4297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO 00/32137 A1 | 6/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO 02/024080 A2 | 3/2002 |
| WO | WO 02/35980 A2 | 5/2002 |
| WO | WO 02/039880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO 2004/019788 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

Chang, Craig G. M.D.[1], et al.. *Gastro-Clip® Gastroplasty: A Very Long-Term Complication, Obesity Surgery*, 14, © FD-Communications Inc.. 2004.

Endo Gia Universal, Single UseStapler and Endo Gia Roticulator, Brochure, 8 pages, Undated.

Filipi, Charles J. M.D., et al., Transoral, *Flexible Endoscopic Suturing for Treatment of GERD: A Multicenter Trial*, Gastrointestinal Endoscopy,. vol. 53, No. 4, pp. 416-422, 2001.

Guidant. Internet. AXIUS™ Vacuum 2 Stabilizer Systems, Internet Website—www.guidant.com/products/axius_vacuum.shtml, 8 pages, visited May 27, 2003.

Gukovsky-Reicher, S., M.D. et al., *Expandable Metal Esophageal Stents: Efficacy and Saftey Review of Current Literature Data and of 53 Stents Placed at Harbor-UCLA Medical Center*, www.medscape.com/viewarticle/423508_print pp. 1-20, Medscape General Medicine 4(1), 2003 © 2002 Medscape, downloaded Oct. 9, 2006.

Hepworth, Clive C. FRCS et al., *Mechanical Endoscopic Methods of Haemostasis for Bleeding Peptic Ulcers: A Review, Bailliere's Clinical Gastroenterology*, vol. 14, No. 3 pp. 467-476, 2000.

Ikeda, Y. et al., *New Suturing Device for Transanal Endoscopic Microsurgery*, Blackwell Science Ltd. p. 1290, 1997.

Johnson & Johnson Gateway[SM] Endopath 3mm, 5mm and 10 mm Diameter Endoscopic Instruments, Internet Website—www.inigateway.com/home.ihtml?loc=USENG&page=viewContent&parentId-0900..., 3 pages, visited May 29, 2003.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor (class I, 878.4800), Appendix F.f, Undated.

Swain, C. Paul, M.D. et al., *An Endoscopic Sewing Machine*, Gastrointestinal Edoscopy, vol. 32, No. 1 pp. 36-38 1986.

Swain, C. Paul, M.D., *Endoscopic Sewing and Stapling Machines*, Endoscopy pp. 205-210, © Georg Thieme Verlag Stuttgart, New York, 1997.

Swain, C. Paul, M.D. et al., *An Endoscopic Stapling Device: The Development of a New Flexible Endoscopically Controlled Device for Placing Multiple Transmural Staples in Gastrointestinal Tissue*, Gastrointestinal Endoscopy, vol. 35, No. 4, pp. 338-339, 1989.

Swain, C. Paul, M.D., *Endoscopic Suturing, Bailliere's Clinical Gastroenterology*, Bailliere's Tindall,, vol. 13 No. 1, pp. 97-108, 1999.

Benjamin, S.B., et al., *A Double-Blind Cross Over Study of the Garren-Edwards anti-Obesity Bubble*m Abstract Submitted to A/S/G/E/ 1987, Georgetown University Hospital and Fairfax Hospital, Washington, D.C. and Fairfax, VA.

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., *Small Intestinal Obstruction Secondary to Obturation by a Garren Gastric Bubble*, The American Journal of Gastroenterology, vol. 82, No. 1, pp. 51-53, 1987.

Cass. O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Clark, Charlene, R.N., *The Gastric Bubble: Medicine, Magic or Mania? SGA Journal*, vol. 9, No. 2, pp. 45-47, Fall 1986.

Cummings, David E., M.D., et al., *Plasma Ghrelin Levels After Diet-Induced Weight Loss or Gastric Bypass Surgery*, New England Journal of Medicine, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., *Evolving Concepts of Reflux: The Ups and Downs of the LES*, Canadian Journal of Gastroenterology, vol. 16, No. 5, pp. 327-331, 2002.

De Waele, B., M.D., et al., *Intragastric Balloons for Preoperative Weight Reduction, Obesity Surgery*, vol. 10, pp. 58-60, 2000.

Edell, Steven L., et al., *Radiographic Evaluation of the Garren Gastric Bubble, American Journal of Radiology*, vol. 145, pp. 49-50, Jul. 1985.

Gray, Henry, R.R.S., *Anatomy of the Human Body, The Digestive System*, Thirtieth American Edition, pp. 1466-1467 (Undated).

Kirby, Donald F., *Incomplete Small Bowel Obstruction by the Garren-Edwards Gastric Bubble Necessitating surgical Intervention*, The American Journal of Gastroenterology, vol. 82, No. 3, pp. 251-253, 1987.

Nieben, Ole Gyring, et al., *Intragastric Balloon as an Artificial Bezoar for Treatment of Obesity*, The Lancet, pp. 198-199, Jan. 23, 1982.

Percival, Walter L., M.D., *"The Balloon Diet": A Noninvasive Treatment for Morbid Obesity. Preliminary Report of 1908 Patients*, The Canadian Journal of Surgery, vol. 27, No. 2, pp. 135-136.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Taylor, T. Vincent, et al., *Gastric Balloons for Obesity, The Lancet*, Abstract, Mar. 27, 1982.

Vandenplas, Y., et al., *Intragastric Balloons in Adolescents with Morbid Obesity*, European Journal of Gastroenterology & Hepatology, vol. 11, No. 3, pp. 243-245, 1999.

Villar, Hugo V., M.D., et al., *Mechanisms of Satiety and Gastric Emptying After Gastric Partitioning and Bypass, Surgery*, pp. 229-236, Aug. 1981.

Wullstein, C., et al., *Compression Anastomosis (AKA-2) in Colorectal Surgery: Results in 442 Consecutive Patients*, British Journal of Surgery 2000, pp. 1071-1075.

Application for U.S. Letters U.S. Appl. No. 10/773,883, filed Feb. 5, 2004 unpublished; Inventors: Gerbi et al.

Application for U.S. Letters U.S. Appl. No. 10/797,439, filed Mar. 9, 2004 unpublished; Inventors: Weller et al.

\* cited by examiner

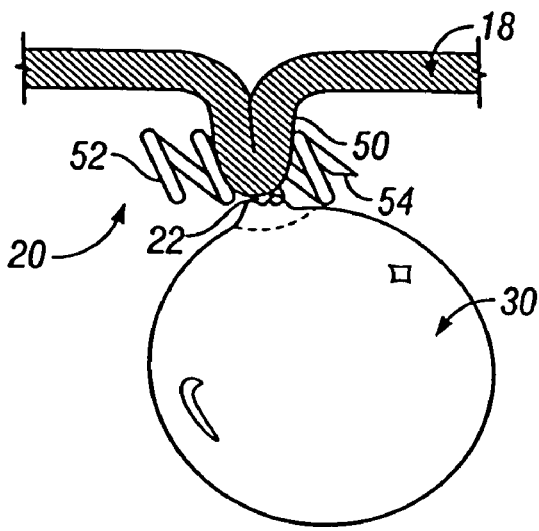
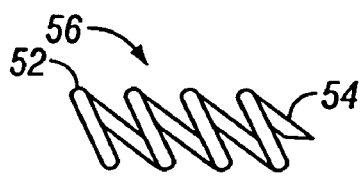
FIG. 4B
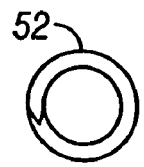
FIG. 4C
FIG. 4A
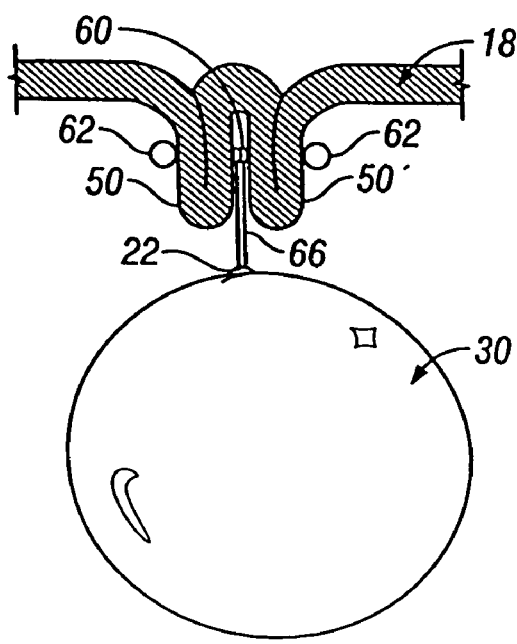
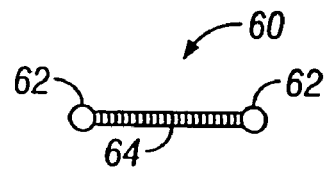
FIG. 5B
FIG. 5A

INTRA-GASTRIC FASTENING DEVICES

CROSS-REFERENCE TO RELATED APPLICATIONS

This application is a continuation of U.S. application Ser. No. 10/394,832 filed Mar. 21, 2003, now U.S. Pat. No. 6,994,715, which is a continuation of U.S. Ser. No. 10/215,070 filed Aug. 7, 2002 now U.S. Pat. No. 6,746,460 which issued Jun. 8, 2004.

FIELD OF THE INVENTION

The present invention relates generally to medical apparatus and methods. More particularly, the present invention relates to devices and methods for the attachment of expandable devices and the like within a patient's body cavity, such as the stomach, intestine or gastrointestinal tract.

BACKGROUND OF THE INVENTION

In cases of severe obesity, patients may undergo several types of surgery either to tie off or staple portions of the large or small intestine or stomach, and/or to bypass portions of the same to reduce the amount of food desired by the patient, and the amount absorbed by the intestinal tract. Procedures such as laparoscopic banding, where a device is used to "tie off" or constrict a portion of the stomach, or the placement of intra-gastric balloons can also achieve these results.

Endoscopic procedures that have been used to assist weight loss have been primarily focused on the placement of a balloon or other space-occupying device in the patient's stomach to fill portions of the stomach to provide the patient with the feeling of fullness, thereby reducing food intake. To accomplish these procedures, an endoscope is utilized to guide the balloon through the patient's mouth and down the esophagus to the stomach. Usually these procedures have allowed placement of the device for 6-12 months, and are coupled with counseling and other types of psychological support.

Many of the conventional surgical interventions require the patient to submit to an intervention under general anesthesia, and can require large incisions and lengthy recovery time. The less invasive procedures, although clinically efficacious in many cases, suffer from complications ranging from deflation of the devices to insufficient anchoring of these devices resulting in unsustained weight loss, stomach erosion, bowel obstruction and even death.

Many of these devices are neither robust enough nor are they adequately secured within the stomach to sustain long term implantation. As a result, many implanted devices are implanted in such a manner as to remain unattached or free-floating within the stomach. Further, due to the caustic nature of stomach acids and other factors, many of the implants deflate and migrate into the intestine, causing bowel obstructions and in some cases death. Also, many devices are not well designed for removal, leading to additional technical difficulties for the clinician.

BRIEF SUMMARY OF THE INVENTION

The present invention provides for the improved methods and apparatus for implanting and anchoring space-occupying devices into the gastrointestinal system of a patient, e.g., the stomach of the patient, that can be deployed in a minimally invasive manner such as transesophageal endoscopy. The invention allows greater access to procedures and devices by patients who might not otherwise be treated surgically as "morbidly obese" (at or above a Body Mass Index (BMI) of 40 kg/m3), but who may just be moderately obese or overweight (BMI of between 25 to 40 kg/m3). In addition, patients who require more invasive surgery for an unrelated ailment, may need a minimally invasive way to lose the weight prior to their more invasive procedure, thereby reducing the risks associated with general anesthesia, or otherwise enabling the more invasive procedure.

Expandable devices that may be inserted into the stomach of a patient may be maintained within the stomach by anchoring or otherwise fixing the device to the stomach wall of the patient. Such expandable devices, e.g., an inflatable balloon, may comprise two portions, an inner portion and an outer portion, the inner portion being able to maintain its shape, regardless of the integrity of the outer portion. Other expandable balloon devices which may be used may maintain their expanded shape and desired volume, independent of any small leaks that may develop over time or they may be configured to maintain a volume of the space-occupying device which can be adjusted in-situ, to change the size of the device after implantation.

The space-occupying devices preferably have a tethering region for attachment to one or more fasteners. The fasteners are configured such that portions of the fasteners may extend at least partially through one or several folds of the patient's stomach wall, thereby maintaining the device within the patient's stomach, but do not extend external to the patient's body. The fasteners may thus be affixed to the stomach walls by deploying the fasteners and manipulating the tissue walls entirely from the inside of the organ.

Such fasteners may be formed in a variety of configurations, e.g., helical, elongate, ring, clamp, and they may optionally be configured to be non-piercing. For example, sutures may simply be used to wrap around or through a tissue fold for tethering the space-occupying devices. Alternatively, non-piercing biased clamps may also be used to tether the device within the stomach.

BRIEF DESCRIPTION OF THE DRAWINGS

FIG. 4A shows a variation of a helically-shaped fastener which has been positioned within the tissue fold for anchoring the space-occupying member.

FIGS. 4B and 4C show side and end views, respectively, of the fastener of FIG. 4A.

FIG. 5A shows another variation of an elongate fastener which has been positioned within multiple tissue folds.

FIG. 5B shows a side view of the fastener of FIG. 5A.

DETAILED DESCRIPTION OF THE INVENTION

Figure 1:
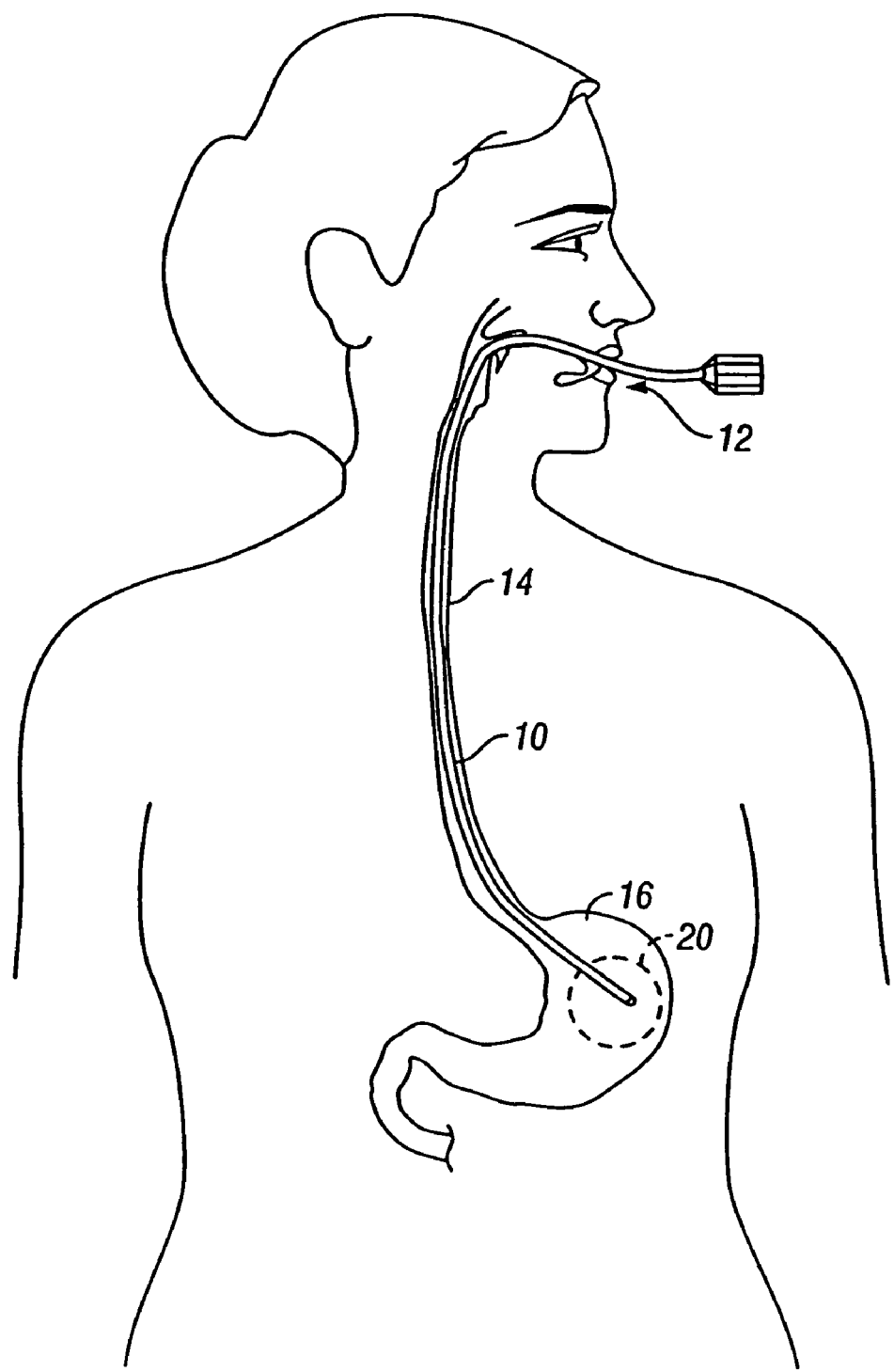
FIG. 1 shows a schematic illustration of a delivery endoscope advanced to a region of interest within the stomach of a patient.

Expandable devices that may be inserted into the stomach of a patient may be maintained within the stomach by anchoring the device to the walls of the stomach using intra-gastric fasteners. Although the fastening devices described herein describe anchoring within a stomach, this is merely illustrative and the fasteners may be utilized in any hollow body organ or interior body space for temporarily or permanently anchoring expandable devices to tissue. FIG. 1 illustrates a delivery endoscope 10 which may be used to deliver the expandable devices as well as the fastening devices into, e.g., stomach 18 of a patient. Endoscope 10 is shown as having been advanced through the mouth 12 and esophagus 14 of the patient to position the distal end of endoscope 10 within a region of interest 20 within stomach 16. As shown in FIGS. 1-3, the region of interest 20 can be remote from the junction between the stomach 16 and the esophagus 14.

Figure 2A:
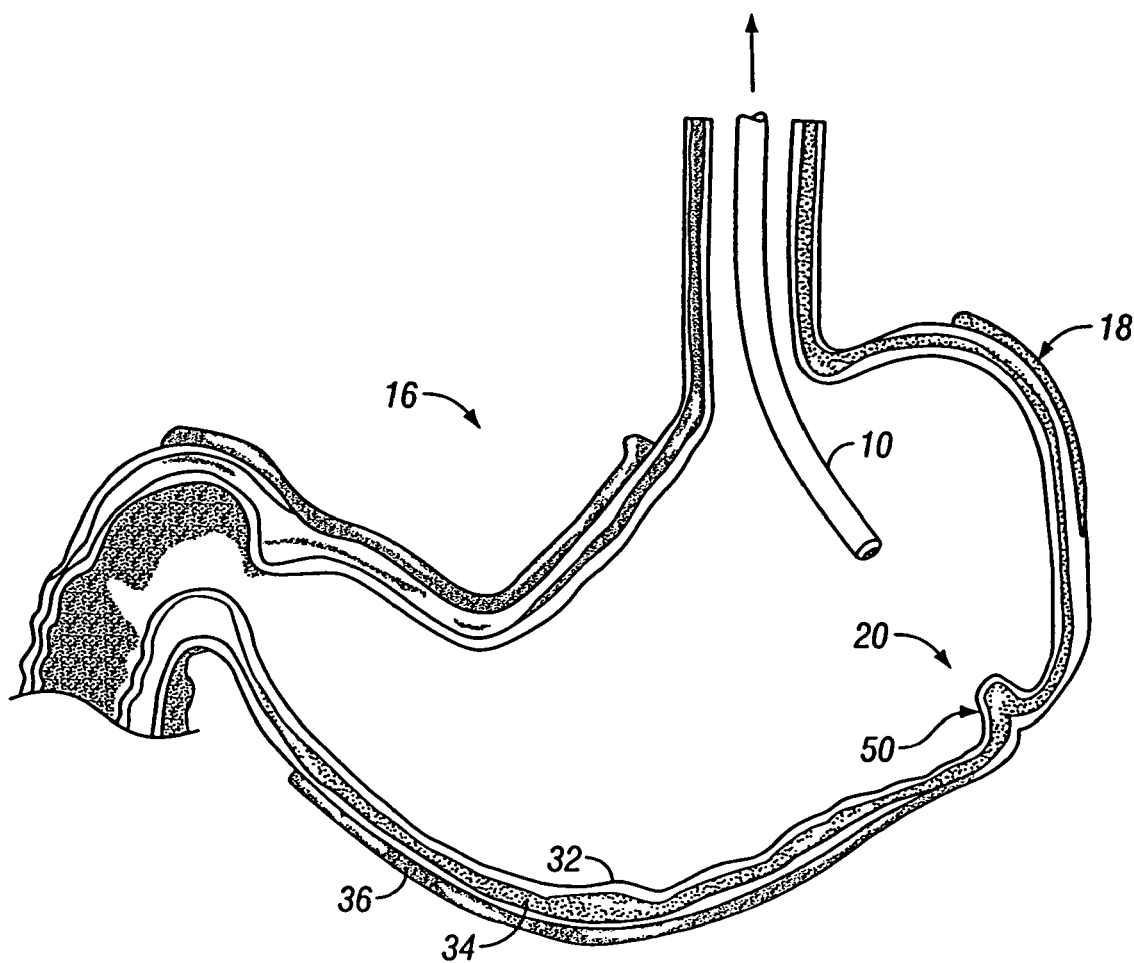
FIG. 2A shows a cross-sectional view of a stomach within which a tissue fold has been formed from the walls of the stomach.
Figure 3:
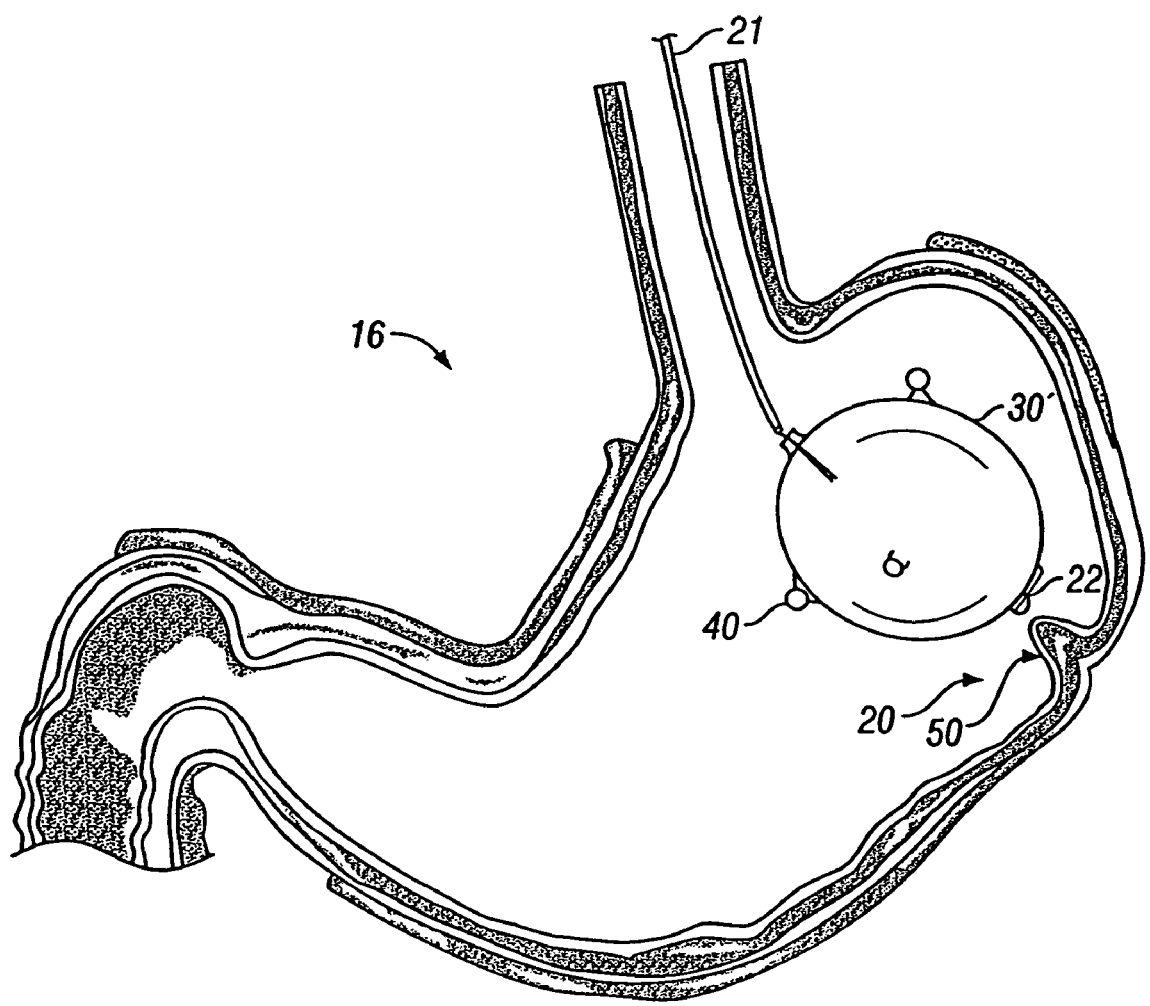
FIG. 3 shows the stomach of FIGS. 2A and 2B in which the space-occupying member has been expanded for deployment.

FIG. 2A shows a cross-sectional view of stomach 16 within which endoscope 10 has been positioned adjacent to region of interest 20. At least one tissue fold 50 is formed from within the lumen of stomach 16 utilizing any number of conventional tools which may be passed through the working channel of endoscope 10, or any of the tissue acquisition devices as described in further detail in U.S. patent application Ser. No. 09/871,297 filed May 30, 2001 or U.S. patent application Ser. No. 10/188,547 filed Jul. 2, 2002, both of which are commonly owned and are incorporated herein by reference in their entirety.

The tissue layers of stomach 16 are comprised of the mucosal layer 32, the muscularis or fibrous muscular layer 34, and the serosal layer 36. In preferably forming tissue fold 50, at least two layers of stomach tissue are folded to contact itself such that a certain amount of fibrous tissue overlap occurs prior to fastening tissue fold 50 in a configuration akin to a lap joint. The amount of the overlap can vary and needs only to be sufficient enough to result in joining of the fastened sections, thereby creating a tissue bridge along the length of the fastened tissue. The tissue bridge may be formed of various layers of the stomach and may include scar tissue and other elements of effective wound healing. Once tissue fold 50 has been desirably configured, a fastener or anchor (as described in further detail below) may be used to maintain the tissue fold configuration for anchoring a space-occupying device thereto.

Figure 2B:
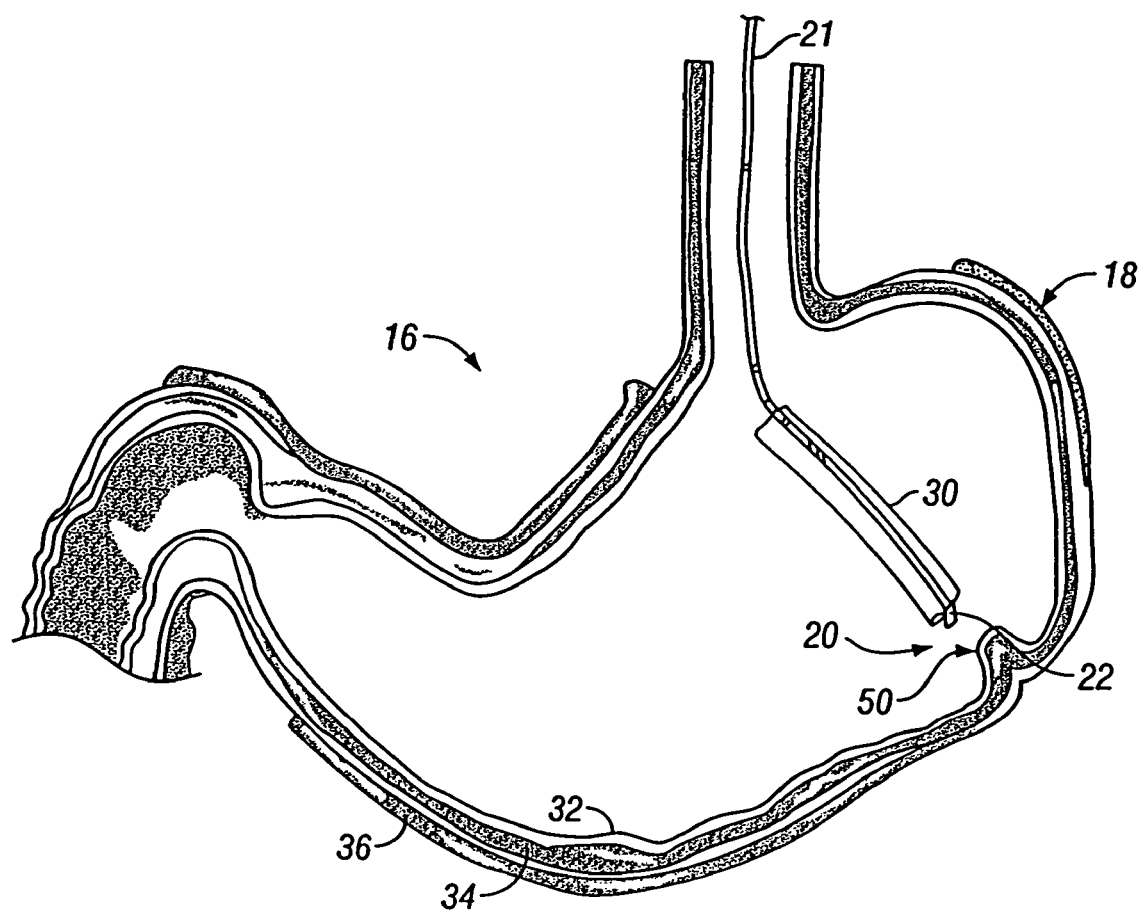
FIG. 2B shows the stomach of FIG. 2A in which an inflatable or space-occupying member (in its deflated or unexpanded state) has been advanced for anchoring to the tissue fold.

Once tissue fold 50 has been formed, the space occupying device, e.g., an expandable scaffold, an inflatable balloon, etc., may be advanced within stomach 16 towards the region of interest 20 for anchoring to tissue fold 50. As shown in FIG. 2B, space-occupying member 30 may be advanced using an elongate delivery member 21, e.g., endoscope 10 or any one of the delivery devices as shown and described in U.S. patent application Ser. No. 09/816,850 filed Mar. 23, 2001, which is commonly owned and is incorporated herein by reference in its entirety. The use of an inflatable balloon in these examples is intended to be illustrative and any number of space-occupying devices, such as an expandable scaffold, may be utilized as described in the incorporated application. Space-occupying member 30 may have a tethering region 22 integrated on its distal end in the shape of, e.g., a tethering ring or clasp, for attachment to the fastener or anchor which maintains tissue fold 50. During delivery, space-occupying member 30 may be advanced transorally in its deflated state using delivery member 21. Delivery member 21 may also be used to deliver an inert inflation fluid, e.g., water, saline, etc., or an inert gas, e.g., nitrogen, air, etc., through a lumen defined within member 21 for expanding space-occupying member 30 during deployment.

As seen in FIG. 3, delivery member 21 may be used to inflate space-occupying member 30 into its expanded shape 30'. The surface of space-occupying member 30' may have one or several tabs 40 extending from or defined along its outer surface to allow a grasping tool to manipulate or remove space-occupying member 30' during the procedure or post-procedurally. Space-occupying member 30 may be affixed to tissue fold 50 by attaching tethering region 22 to the fastener or anchor which maintains tissue fold 50. The attachment may be accomplished prior to, during, or even after inflation or expansion of member 30 and may be done by any number of manipulation tools endoscopically or laparoscopically delivered and positioned, as appreciated by one skilled in the art.

Space-occupying member 30 may be formed of a urethane interior and a silicone exterior. The urethane provides a durability to the balloon for resisting undesirable rupture or leakage and the silicone exterior provides for a smoothness, and conformability to avoid unnecessary trauma or irritation to the stomach lining. In another variation, the member 30 is formed of a composite of silicone, aluminized polyester film, and polyethylene. In this variation, the space occupying device is formed by heat-sealing sheets of mylar/polyethylene composite. The seam is then trimmed to a minimum size and a valve attached. The assembly is then dipped in room temperature vulcanizing (RTV) liquid silicone which, once cured, will leave a smooth surface, which may or may not have a palpable seam. Alternatively, the space occupying device can be rotated as the silicone cures, to allow for a more consistent coating to form.

A variety of sizes and shapes of space-occupying member 30 are contemplated, and it is to be appreciated that one skilled in the art would be competent to choose a particular shape and size according to the particular application. The space-occupying member 30 can be, for example, a spherical or ellipsoidal balloon or another suitable shape. In the case of an ellipsoidal balloon, one method of anchoring such a balloon is along the longer axis of the balloon; however, anchoring may also be achieved by anchoring along the shorter axis of the balloon. Balloon volumes can vary, but a typical volume is approximately 500 cubic centimeters (cc).

FIGS. 4A to 4C show various views of one variation of an anchoring device which may be utilized to maintain the configuration of tissue fold 50 as well as to affix space-occupying member 30 to tissue fold 50. FIG. 4A shows a side view of a helically-shaped fastener 52 pierced through tissue fold 50. Variation 52 is a fastener having a plurality, i.e., more than one, of helical coils 56, as shown in the side view of fastener 52 in FIG. 4B. Fastener 52 preferably has a distal tip 54 which is sharpened to facilitate piercing into and advancement through tissue fold 50 while being rotatingly advanced. FIG. 4C shows an end view in which fastener 52 is preferably formed into a circular configuration to provide for smooth advancement and rotation into the tissue, although other shapes such as elliptical are contemplated. It is to fastener 52 that tethering region 22 may be affixed directly or by using a biocompatible connecting member, e.g., a suture.

Fastener 52 is shown as having helical coils 56 at a uniform pitch. However, fastener 52 may be modified such that the pitch of helical coils 56 is non-uniform. In such a variation, the location along coils 56 where the tissue is ultimately compressed may have a pitch which is tighter or higher than the rest of fastener 52. The tighter pitch allows for increased tissue compression along that portion of fastener 52. The remaining helical coils 56 may have a lower or looser pitch to facilitate insertion into the tissue.

Fastener variation 52, as well as other fastening devices described herein, are preferably made of metallic or non-metallic biocompatible materials. Such materials may include stainless steels, nickel alloys, and titanium alloys, as well biocompatible plastics. Moreover, any of the fasteners may additionally be coated with a healing agent or anti-bacterial agent to facilitate tissue growth and healing.

Additionally, the fasteners may have a cutting, abrading, scoring, heating, freezing, chemically damaging, or some other damaging surface where it contacts the tissue. This scoring or roughening may damage the interior lining of the tissue contacting each other. This damage may encourage a more vigorous healing response and a more permanent fixation between the damaged tissue once stapled or affixed together. Detailed examples may be found in U.S. patent application Ser. No. 09/871,297 filed May 30, 2001, which is commonly owned and is incorporated herein by reference in its entirety.

FIGS. 5A and 5B show another variation of an anchoring device. In this variation, another tissue fold 50' in addition and adjacent to tissue fold 50 may be utilized. Although two tissue folds are shown, any number of folds may be used as practicable depending upon the desired results and anchoring configuration. Fastener variation 60 may include a straight member having rounded ends 62 to facilitate the anchoring placement and positioning within tissue folds 50, 50'. As shown in FIG. 5B, the length of fastener 60 may be textured 64 to improve tissue healing as well as to prevent excessive fastener movement once positioned within the tissue. Space-occupying member 30 may be attached to fastener 60 using tether or connecting member 66, which may be a suture or a rigid connecting pin.

Figure 6:
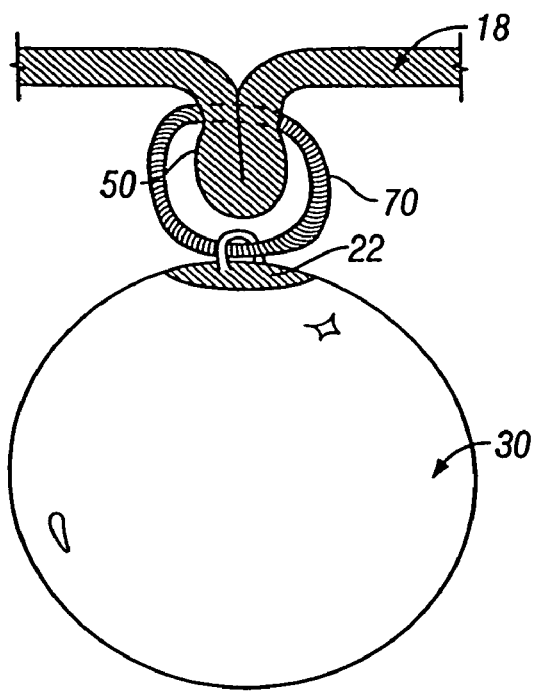
FIG. 6 shows another variation of a ring-shaped fastener which has been positioned within the tissue fold.

Another tissue-piercing fastener variation is shown in FIG. 6, which shows a ring-shaped fastener 70 which may pierce tissue fold 50 and connect to tethering region 22 of space-occupying member 30. Ring 70 may be formed as a C-clip type fastener which is biased to remain a closed loop but which may be urged open during deployment. A partial length or the full length of ring 70 surface may be textured, as described above. Moreover, a single ring 70 or several rings may be deployed within the tissue to anchor to the same space-occupying member 30 or to multiple members 30, depending upon the desired results and configuration.

Figure 7A:
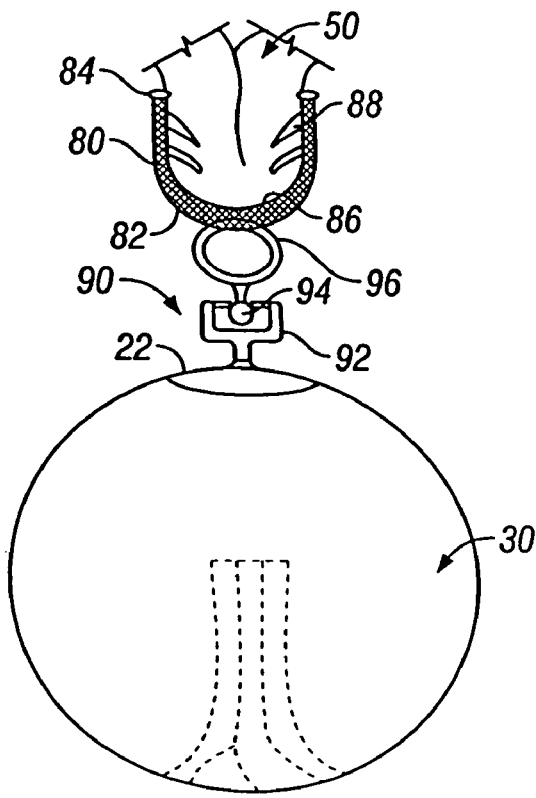
FIG. 7A shows an end view of another variation of a clamp fastener.
Figure 7B:
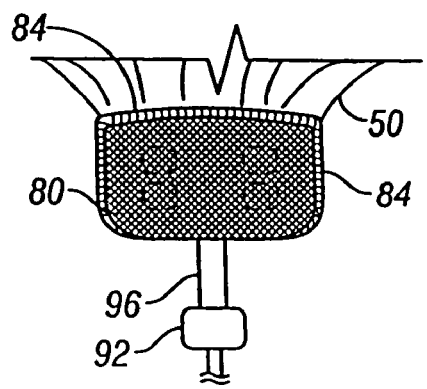
FIG. 7B shows a side view of the clamp fastener of FIG. 7A.

Yet another variation of the fastener is shown in FIGS. 7A and 7B. FIG. 7A shows an end view of clamp fastener 80 which is comprised of two opposed clamp members which are preferably biased towards one another about a hinge portion 82. Fastener 80 may be made of a spring stainless steel or a shape memory alloy, e.g., nickel-titanium alloy, and may be pre-configured into its clamp configuration. As shown in FIGS. 7A and 7B, edges 84 may have beads attached around the entire periphery of the clamp or partially thereon either by an adhesive or by forming the beads integrally with the clamp 80. Alternatively, edges 84 may be blunted during manufacturing to provide atraumatic edges for presentation to the tissue surface.

Clamp 80 may be formed in a variety of shapes, e.g., in a binder clip configuration, a "taco" shell configuration, etc., or any other shape which provides contact surfaces 86 having a contact area sufficient to enable secure anchoring to the tissue. Contact surfaces 86 may be formed with additional anchoring devices such as barbs 88, surface texturing, and/or felt or another tissue in-growth-promoting material. If barbs 88 are used, any number may be used in a variety of barb configurations, e.g., angled barbs, etc.

To affix space-occupying member 30 to fastener 80, a rotating joint 90 may be used. In this variation, clamp 80 may have attached connector 96 having a balled pivot 94 at a distal end. Tethering region 22 of space-occupying member 30 may have a receiving ring for rotatingly receiving pivot 94. Joint 90 may be utilized on any of the fasteners described herein and allows space-occupying member 30 to rotate freely about the joint without regards to the orientation of clamp 80. This may aid in minimizing tissue tears and excess stress applied to tissue fold 50 as space-occupying member 30 is moved about. To deploy clamp 80, it may be urged into an "open" configuration as it is advanced over tissue fold 50 by the delivery device. Once in position over the tissue, clamp 80 may then be released allowing it to compress upon the tissue to become affixed to tissue fold 50.

Figure 8:
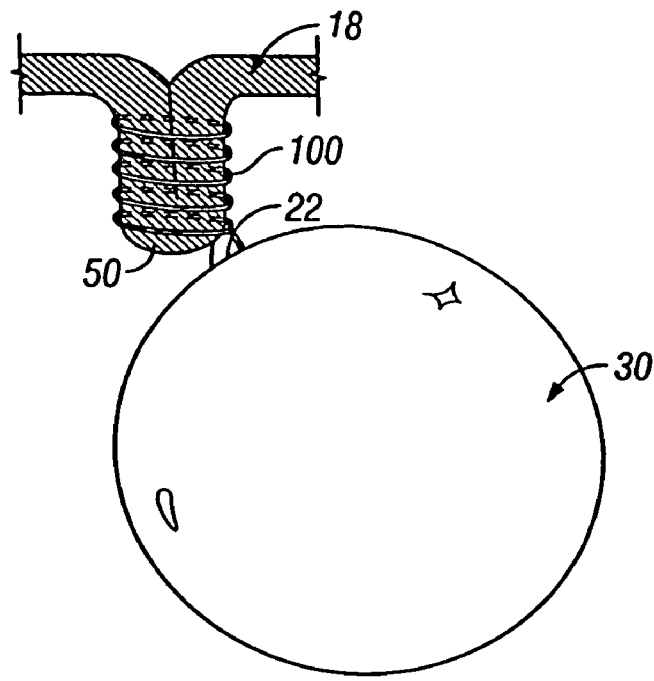
FIG. 8 shows another variation in which a piercing or non-piercing suture is used as a fastener for anchoring the space-occupying member to the tissue.

Another fastener variation 100 is shown in FIG. 8. Suture 100 may simply be used to wrap around tissue fold 50. In this variation, suture 100 may be optionally pierced through the tissue or it may simply be wrapped a number of times around tissue fold 50 to affix space-occupying member 30. Suture 100 may be made of any suitable material, e.g., stainless steel, nylon, polypropylene, or any other conventional suturing material.

Figure 9A:
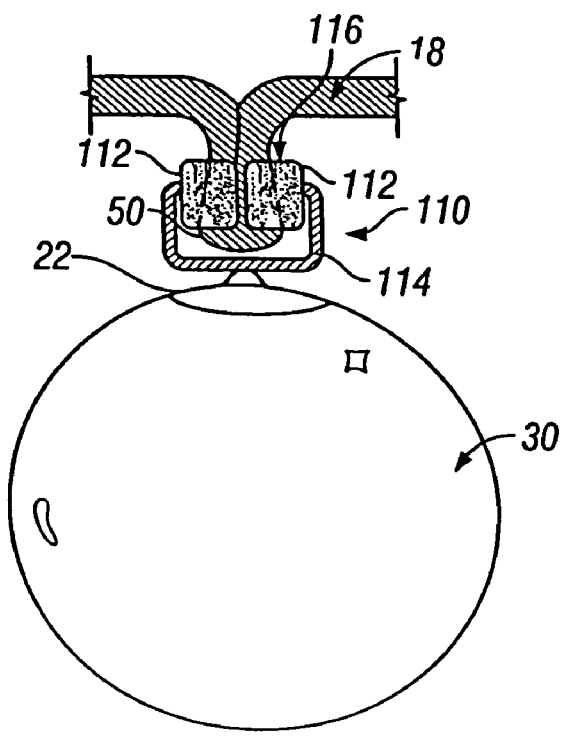
FIG. 9A shows yet another variation of a clamp fastener.
Figure 9B:
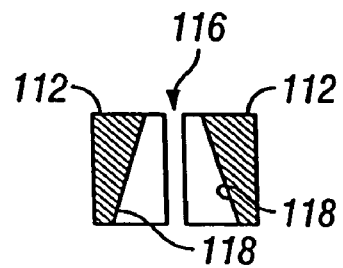
FIGS. 9B and 9C show cross-sectional side and end views, respectively, of the clamp fastener of FIG. 9A.
Figure 9C:
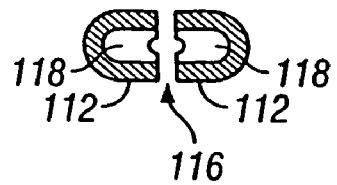

Yet another variation is shown in FIGS. 9A to 9C of a non-piercing clamp fastener 110. Fastener 110 in this variation is comprised of at least two opposed collar portions 112 which are connected by a biasing connecting member 114. Member 114 is preferably configured to provide a biasing force such that portions 112 are urged towards one another. Collar portions 112 collectively define a receiving channel 116 through which tissue fold 50 may be positioned and held. Contact walls 118 of receiving channel 116 may be smooth and non-piercing, but they may optionally have a number of teeth or barbs which project into channel 116 for completely or partially penetrating the tissue held therewithin. Moreover, contact walls 118 may have its area varied depending upon the shape and area of the tissue surface presented. For instance, if the tissue area for attachment is formed in the shape of a uvula, then the area of contact walls 118 may be minimized and optionally tapered to receive the bulging contact tissue. If the tissue area is formed more as a fold of tissue, the area of contact walls 118 may be enlarged to present a larger contact region to the tissue, as in the variation of FIGS. 7A and 7B.

With the collar portions 112 clamping onto tissue fold 50, suitable grasping or holding pressure is applied by the fasteners to maintain attachment to tissue fold 50. If too much pressure is applied, the tissue 50 being compressed may necrose, but if too little pressure is applied, slippage of fastener 110 may occur. Accordingly, the suitable amount of pressure may be determined by one of skill in the art depending upon factors such as the size of tissue fold 50 and the size of fastener 110, among other factors.

Although preferred illustrative variations of the present invention are described above, it will be evident to one skilled in the art that various changes and modifications may be made without departing from the invention. For instance, variations of the present invention may be used as permanent or temporary anchoring devices. Moreover, modified variations may also be used in other regions of the body, e.g., for use in the intestinal tract, etc. It is intended in the following claims to cover all such changes and modifications that fall within the true spirit and scope of the invention.

We claim:

1. A method of placing an anchor to a region of tissue within a hollow body organ, comprising:
   grasping the region of tissue from an interior surface of the hollow body organ;
   configuring the region of tissue to create at least two folds of tissue;
   securing an anchor to the folds of tissue such that the folds of tissue contain a certain amount of fibrous tissue thereby creating a tissue bridge to maintain the tissue fold configuration; and
   attaching an expandable, inflatable device to the anchor;
   wherein the region of tissue is remote from a junction between the hollow body organ and an esophagus.

2. The method of claim 1, further comprising advancing an endoscope transorally to the region of tissue.

3. The method of claim 1, wherein the hollow body organ comprises a stomach.

4. The method of claim 1, wherein grasping the region of tissue comprises holding the tissue with a vacuum force.

5. The method of claim 1, wherein grasping the region of tissue comprises holding the tissue mechanically.

6. The method of claim 1, wherein the anchor is a suture.

7. The method of claim 1, wherein the anchor comprises at least one protrusion adapted to extend within the tissue.

8. The method of claim 1, wherein the anchor is a staple.

9. A method of placing an anchor to a region of tissue within a hollow body organ, comprising:
   grasping the region of tissue from an interior surface of the hollow body organ;
   configuring the region of tissue to create at least two folds of tissue;
   securing an anchor to the folds of tissue thereby creating a tissue bridge to maintain the tissue fold configuration; and
   attaching a balloon to the anchor;
   wherein the region of tissue is remote from a junction between the hollow body organ and an esophagus.

10. A method of placing an anchor to a region of tissue within a hollow body organ, comprising:
   grasping the region of tissue from an interior surface of the hollow body organ;
   configuring the region of tissue to create at least two folds of tissue;
   securing an anchor to the folds of tissue thereby creating a tissue bridge to maintain the tissue fold configuration;
   attaching a tether to the anchor; and
   attaching a balloon to the tether so that the balloon can float freely in the hollow body organ;
   wherein the region of tissue is remote from a junction between the hollow body organ and an esophagus.

* * * * *